US00PP18891P2

(12) United States Plant Patent
Kraan

(10) Patent No.: US PP18,891 P2
(45) Date of Patent: Jun. 3, 2008

(54) ROSE PLANT NAMED 'BOKRASKATE'

(50) Latin Name: *Rosa hybrida*
Varietal Denomination: Bokraskate

(75) Inventor: Kees Jan Kraan, Ter Aar (NL)

(73) Assignee: Boot & Co. Nurseries BV, Boskoop (NL)

( * ) Notice: Subject to any disclaimer, the term of this patent is extended or adjusted under 35 U.S.C. 154(b) by 0 days.

(21) Appl. No.: 11/602,932

(22) Filed: Nov. 21, 2006

(51) Int. Cl.
*A01H 5/00* (2006.01)

(52) U.S. Cl. ..... Plt./108

(58) Field of Classification Search ..... Plt./107, Plt./108

See application file for complete search history.

*Primary Examiner*—Annette H Para

(57) ABSTRACT

A new cultivar of *Rosa* plant named 'Bokraskate' that is characterized by a short dense habit, few spines and scarlet-red flowers with deep red hips.

1 Drawing Sheet

Botanical classification: *Rosa hybrida.*
Variety denomination: 'Bokraskate'.

BACKGROUND OF THE INVENTION

The present invention relates to a new and distinct cultivar of Rose plant botanically known as *Rosa* and hereinafter referred to by the cultivar name 'Bokraskate'.

The new cultivar is the product of a breeding program conducted by the inventor in a cultivated area of Boskoop, The Netherlands. The objective of the breeding program was to develop a new rose with a short dense habit and interesting flower colors. 'Bokraskate' is a hybrid that originated from the hybridization of the female or seed parent *Rosa* 'Bokrahan' (not patented) and the male or pollen parent, an unnamed proprietary seedling. The cultivar 'Bokraskate' was selected by the inventor in the Summer of 2000 as a single plant within the progeny of the stated cross in a controlled environment of Boskoop, The Netherlands.

The closest comparison plant is the female parent *Rosa* 'Bokrahan'. 'Bokraskate' is distinguishable from 'Bokrahan' by a shorter and more spreading habit and fewer spines. The new cultivar 'Bokraskate' is distinguishable from the male parent in having fewer spines and a low spreading habit.

Asexual reproduction by cuttings of the new cultivar 'Bokraskate' was first performed in 2002 in Boskoop, The Netherlands by the inventor. Since that time, under careful observation, the unique characteristics of the new Rose cultivar have been uniform, stable and reproduced true to type in successive generations of asexual reproduction.

SUMMARY OF THE INVENTION

The following represent the distinguishing characteristics of the new *Rosa* cultivar 'Bokraskate'. These traits in combination distinguish 'Bokraskate' as a new and distinct cultivar apart from all other existing varieties of *Rosa* known to the inventor. 'Bokraskate' has not been tested under all possible conditions and phenotypic differences may be observed with variations in environmental, climatic, and cultural conditions, however, without any variance in genotype.

1. *Rosa* 'Bokraskate' exhibits a short dense habit.
2. *Rosa* 'Bokraskate' exhibits few spines.
3. *Rosa* 'Bokraskate' exhibits scarlet-red flowers and deep red hips.

BRIEF DESCRIPTION OF THE DRAWING

The accompanying photographs illustrate the distinguishing traits of *Rosa* 'Bokraskate'.

The plant in the upper photograph is an overall view of one year old field grown plants.

The lower photograph is a close up view of the flowers of 'Bokraskate'.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Rosa* cultivar named 'Bokraskate'. Data was collected in Boskoop, The Netherlands from one year old field grown plants. The time of year was August and the temperatures ranged from 14-32° Centigrade during the day, and 7-14° Centigrade during the night. The light level was natural outdoor light and there were no photoperiodic treatments or growth retardants used. Color determinations are in accordance with The Royal Horticultural Society Colour Chart except where general color terms of ordinary dictionary significance are used. The growing requirements are similar to the species.

Botanical classification: *Rosa hybrida* 'Bokraskate'.
Type: Perennial shrub.
Use: Ornamental.
Parentage: 'Bokraskate' is a hybrid plant that resulted from the hybridization of the following parent plants:
*Female parent.*—*Rosa* 'Bokrahan'.
*Male parent.*—An unnamed proprietary rose seedling.
Vigor: Moderate.
Growth rate: Approximately 12 cm. per month in spring.
Plant shape: Broad-spreading.

Suitable container size: 1-2 liter container.
Height: 38 cm. in height.
Width: 67 cm. in width.
Hardiness: USDA Zone 3.
Propagation: Softwood cuttings.
Time to initiate roots: Approximately 60 days are required to produce roots on an initial cutting.
Crop time: Approximately 12 months are required to achieve a finished plant from an unrooted cutting.
Root system: Fine and fibrous.
Light: Plant in full sun.
Stem:
*Branching habit.*—Moderately free branching.
*Average number of lateral branches.*—Four.
*Stem diameter.*—Approximately 4 mm. in diameter.
*Stem length.*—Approximately 28.9 cm. in length.
*Stem strength.*—Moderately strong.
*Stem color.*—145A.
*Pubescence.*—Young stems densely hirsute. Hairs 1 mm, 145B to 145C.
*Internode length.*—Approximately 2.4 cm. between nodes.
*Shape.*—Rounded, glossy, and covered with very small soft spines.
*Surface.*—Glabrous and dull and covered with sharp spines.
*Number of spines.*—0.4 per square cm.
*Spine dimensions.*—Approximately 9 mm. in length and 7 mm. in width.
*Color of spines.*—Color ranges from 178C to 152A.
Foliage:
*Durability to foliage stresses.*—High.
*Texture.*—Smooth and glossy.
*Leaf arrangement.*—Alternate.
*Compound or single.*—Compound.
*Quantity of leaves per lateral branch.*—Approximately 14.
*Quantity of leaflets per leaf.*—Average 8.
*Leaf margin.*—Serrate.
*Leaf shape.*—Oval.
*Leaf tip.*—Acute.
*Leaf base.*—Rounded.
*Leaf length.*—Leaf, 9.9 cm; leaflet, 3.1 cm.
*Leaf width.*—Leaf, 5.5 cm; leaflet, 1.7 cm.
*Leaf texture.*—Slightly rugose, glossy.
*Pubescence.*—Upper side smooth. Lower side covered with hirsute hair, 0.3 mm; 138B/138C.
*Vein pattern.*—Pinnate.
*Leaf color young, upper surface.*—144A.
*Leaf color young, lower surface.*—143C.
*Leaf color mature, upper surface.*—Between 137A and 147A.
*Leaf color mature, lower surface.*—138B.
*Vein color, upper side.*—143B.
*Vein color, under side.*—145C.
*Leaf attachment.*—Petiolate.
*Petiole dimensions.*—2.0 cm. in length and 1.5 mm. in width.
*Petiole color.*—145A/145B.
*Other.*—Sharp spines 1.4 cm. in length; upper side 144A, lower side 145B; slightly pubescent. Stems sparsely covered with soft spines. Average 12 spines per stem; average length 0.2 mm, average height 1 mm; color 145A.

Flower:
*Flower arrangement.*—Terminal clusters.
*Inflorescence type.*—Clustered.
*Inflorescence height.*—Approximately 6 cm. in height.
*Inflorescence diameter.*—Approximately 9.2 cm. in diameter.
*Quantity of flowers per inflorescence.*—Approximately 5.
*Flower type.*—Single and rotate.
*Flowering habit.*—Once a year form early June to September.
*Quantity of flowers per lateral stem.*—Approximately 2.
*Quantity of flower buds per lateral stem.*—Approximately 3.
*Quantity of flowers and buds per plant.*—Approximately 20.
*Flowering season.*—Early June to September.
*Time to flower (response time).*—Approximately 8 months.
*Rate of flower opening.*—Approximately 40% of the flowers per corymb are opened at once.
*Fragrance.*—Strong and pleasant.
*Flower bud length.*—1.8 cm. in length.
*Flower bud diameter.*—9 cm. in diameter.
*Flower bud shape.*—Ovate.
*Bud color.*—144A.
*Flower aspect.*—Upward to outward.
*Flower shape.*—Rotate.
*Flower dimensions.*—6.1 cm. in diameter and 2.7 cm. in height.
*Flower longevity.*—Lasts a few days on plant.
*Petal color when opening (under side).*—72A.
*Petal color when opening (upper side).*—N74A.
*Petal color fully opened (upper side).*—N74A.
*Petal color fully opened (under side).*—72A.
*Petal color, fading to.*—N74A, margins N74B.
*Petal appearance.*—Rotate.
*Persistent or self-cleaning.*—Self-cleaning.
*Petal texture.*—Glabrous.
*Petal arrangement.*—Rotate.
*Number of petals.*—Five in number.
*Petals fused or unfused.*—Unfused.
*Petal shape.*—Broad obcordate.
*Petal margin.*—Entire.
*Petal apex.*—Shallowly retuse.
*Petal dimensions.*—3 cm. in length and 2.7 cm. in width.
*Petaloids.*—Absent.
*Pedicel dimensions.*—1.5 cm. in length and 1.5 mm. in diameter.
*Pedicel angle.*—20°.
*Pedicel color.*—145A to 145B.
*Pedicel diameter.*—1.5 mm.
*Pedicel strength.*—Strong.
*Sepal color, young (upper side).*—144A to 144B, base 144C.
*Sepal color, young (under side).*—144A.
*Sepal color, mature (upper side).*—144A to 144B, base 144C.
*Sepal color, mature (under side).*—144B, apex 148A.
*Sepal surface.*—Dull and pubescent.
*Sepal arrangement.*—Rotate and reflexed.
*Number of sepals.*—Five.
*Sepal shape.*—Narrow ovate.
*Sepal margin.*—Entire.

*Sepal apex.*—Narrow apiculate.
*Sepal base.*—Broad cuneate.
*Sepal dimensions.*—2 cm. in length and 6 mm. in width.
*Petaloids.*—Absent.
*Calyx shape.*—Rotate.
*Calyx dimensions.*—1.1 cm. in length and 3.6 cm. in diameter.

Reproduction organs:
*Stamen number.*—Approximately 150.
*Anther shape.*—Basifixed, kidney shape.
*Anther dimensions.*—1 mm. in diameter and 7 mm. in length.
*Anther color.*—5C.
*Amount of pollen.*—Moderate.
*Pollen color.*—11A.
*Pistil number.*—35 in number.
*Pistil length.*—1 mm.
*Stigma shape.*—Irregular and flattened.
*Stigma color.*—13C.
*Style length.*—0.6 mm.
*Style color.*—13C.
*Ovary color.*—143B.

Seed: Seed production has not been observed.

What is claimed is:

1. A new and distinct variety of *Rosa* plant named 'Bokraskate' as described and illustrated.

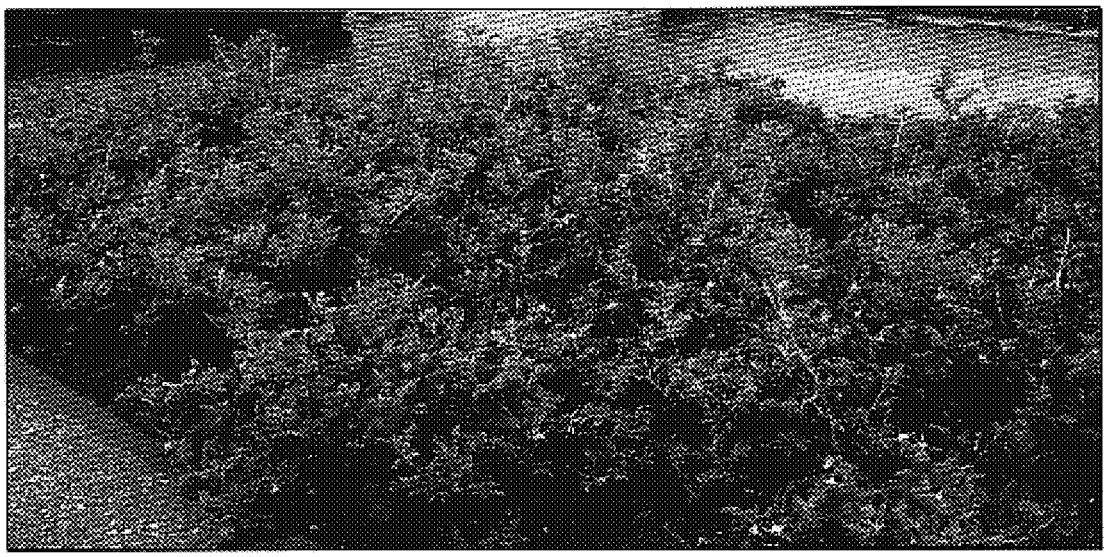
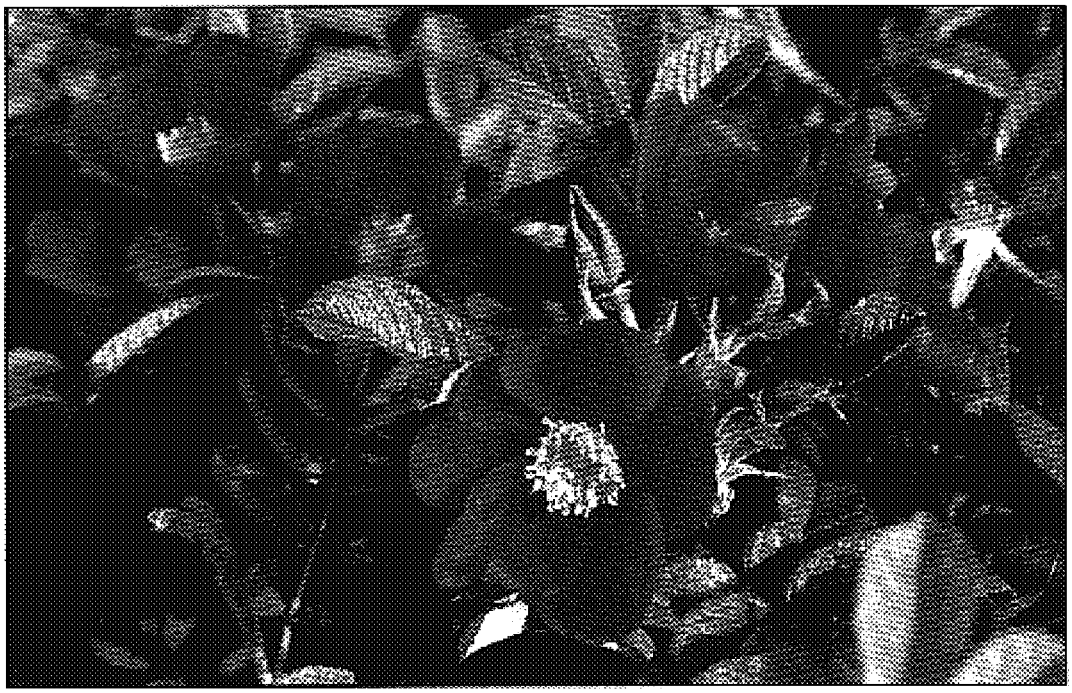

* * * * *